United States Patent
Gewald

(10) Patent No.: US 6,965,029 B2
(45) Date of Patent: Nov. 15, 2005

(54) METHOD FOR PRODUCING ENANTIOMER-FREE 6,8 DIHYDROXY OCTANOIC ACID ESTERS BY MEANS OF ASYMMETRIC, CATALYTIC HYDROGENATION

(75) Inventor: Rainer Gewald, Dresden (DE)

(73) Assignee: Viatris GmbH & Co. KG, Frankfurt am Main (DE)

( * ) Notice: Subject to any disclaimer, the term of this patent is extended or adjusted under 35 U.S.C. 154(b) by 196 days.

(21) Appl. No.: 10/333,812

(22) PCT Filed: Jul. 17, 2001

(86) PCT No.: PCT/EP01/08244

§ 371 (c)(1),
(2), (4) Date: Jan. 27, 2003

(87) PCT Pub. No.: WO02/10113

PCT Pub. Date: Feb. 7, 2002

(65) Prior Publication Data

US 2004/0030178 A1 Feb. 12, 2004

(30) Foreign Application Priority Data

Jul. 27, 2000 (DE) .......................... 100 36 516

(51) Int. Cl.[7] ............................. C07D 471/00
(52) U.S. Cl. .................... 546/39; 549/330; 560/174; 562/587
(58) Field of Search ............... 546/39; 549/330; 560/174; 562/587

(56) References Cited

FOREIGN PATENT DOCUMENTS

| DE | 36 29 116 | 3/1988 |
|---|---|---|
| DE | 197 09 069 | 9/1998 |
| EP | 174057 | 3/1986 |
| EP | 245959 | 11/1987 |
| EP | 256634 | 2/1988 |
| EP | 272787 | 6/1988 |
| EP | 366390 | 5/1990 |
| EP | 0 427 247 | 11/1990 |
| EP | 0 487 986 | 11/1991 |
| EP | 470756 | 2/1992 |
| EP | 643065 | 3/1995 |
| WO | WO 96/01831 | 1/1996 |

OTHER PUBLICATIONS

Yurugi, S et al Yakugaku Zasshi (1960) 80 1170–5 Chem Abst. 55:22762 (1960).*
S.M. Bezbarua et al., *Synthesis*, 1996, vol. 11. pp. 1289–1290.
J.D. Elliott et al., *Tetrahedron Letters*, 1985, vol. 26, No. 21, pp. 2535–2538.
A Baur et al., *Klin. Wochenschr.*, 1991, vol. 69, pp. 722–724.
J.P. Merin et al., *FEBS Letter*, 1996, vol. 394, pp. 9–13.
R. Hermann et al., *Eur. J. Pharmaceut. Sci.*, 1996, vol. 4, pp. 167–174.
G. Raddatz u.H. Bisswanger, *J. Biotechnol.*, 1997, vol. 58, pp. 89–100.
T.M. Hagen et al., *FASEB J.*, 1999, vol. 13, pp. 411–418.
J.S. Yadav et al.,*J. Sci. Ind. Res.*, 1990, vol. 49, pp. 400–409.
E. Walton et al., *J. Am. Chem. Soc.*, 1955, vol. 77, pp. 5144–5149.
D.S. Acker et al., *J. Am. Chem. Soc.*, 1957, vol. 79, pp. 6483–6487.
L.G. Chebotareva et al., *Khim–Farm. Zh.*, 1980, vol. 14, pp. 92–98.
A.S. Gopalan et al., *Tetrahedron Letters*, 1989, vol. 30, No. 42, pp. 5705–5708.
A.G. Tolstikov et al., *Bioorg. Khim.*, 1990, vol. 16, pp. 1670–1674.
L. Dasaradhi et al., *J. Chem. Soc., Chem. Commun.*, 1990, pp. 729–730.
A.S. Gopalan et al.,*J. Chem. Perkin Trans.*, 1990, vol. 1, pp. 1897–1900.
R. Bloch et al., *Tetrahedron*, 1992, vol. 48, pp. 453–462.
B. Adger et al., *J. Chem. Soc. Chem. Commun.*, 1995, pp. 1563–1564.
Y.R. Santosh Laxmi et al., *Synthesis*, 1996, pp. 594–596.
M. Bezbarua et al., *Synthesis*, 1996, pp. 1289–1290.
N.W. Fadnavis et al., *Tetrahedron: Asymmetry*, 1997, vol. 8, No. 2, pp. 337–339.

(Continued)

*Primary Examiner*—Paul J. Killos
(74) *Attorney, Agent, or Firm*—Burns, Doane, Swecker & Mathis, L.L.P.

(57) ABSTRACT

The invention relates to a process for the preparation of compounds of the general formula I

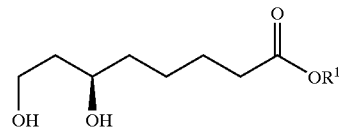

(R)-I

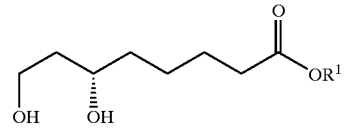

(S)-I in which $R^1$ represents a $C_1$–$C_{20}$-alkyl group, a $C_3$–$C_{12}$-cycloalkyl group, a $C_7$–$C_{12}$-aralkyl group or a mono- or bi-nuclear aryl group, in which a ketone of formula II

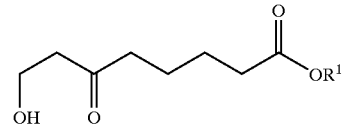

II wherein $R^1$ is as defined above, is subjected to asymmetric hydrogenation.

8 Claims, No Drawings

OTHER PUBLICATIONS

N.W. Fadnavis et al., *Tetrahedron: Asymmetry*, 1998, vol. 9, pp. 4109–4112.
S. Lee et al., *J. Korean Chem. Soc.*, 1999, vol. 43, No. 1, pp. 128–130.
R. Zimmer et al., *Tetrahedron: Asymmetry*, 2000, vol. 11, pp. 879–887.
M.W. Bullock et al., *J. Am. Chem. Soc.*, 1954, vol. 76, pp. 1828–1832.
J. Tsuji et al., *J. Org. Chem.*, 1978, vol. 43, pp. 3606–3607.
J.P. Genet et al., *Tetrahedron: Asymmetry*, 1994, vol. 5, pp. 675–690.
P. Stahly et al., *Organometallics*, 1993, vol. 12, pp. 1467–1470.
R. Noyori et al., *J. Am. Chem. Soc.*, 1980, vol. 102, pp. 7932–7934.
M. Murata et al., *Synlett*, 1991, pp. 827–829.
R. Schmid et al., *Helv. Chim. Acta*, 1988, vol. 71, pp. 897–929.
R. Schmid et al., *Helv. Chim. Acta*, 1991, vol. 74, pp. 370–389.
A. Miyashita et al., *Chem. Lett.*, 1989, pp. 1849–1852.
M. Burk et al., *Organometallics*, 1990, vol. 9, pp. 2653–2655.
M. Burk et al., *J. Am. Chem. Soc.*, 1995, vol. 117, pp. 4423–4424.
B. Bosnich et al., *J. Am. Chem. Soc.*, 1977, vol. 99, pp. 6262–6267.
J.D. Gopalan et al., *Tetrahedron Letters*, 1985, pp. 2535–2538.
M.S. Bezbarua et al., *Synthesis*, 1996, pp. 1289–1290.

* cited by examiner

METHOD FOR PRODUCING ENANTIOMER-FREE 6,8 DIHYDROXY OCTANOIC ACID ESTERS BY MEANS OF ASYMMETRIC, CATALYTIC HYDROGENATION

TECHNICAL FIELD

The present invention relates to a novel process for the preparation of enantiomerically pure 6,8-dihydroxyoctanoic acid esters of the general formula I, wherein $R^1$ represents a $C_1$–$C_{20}$-alkyl group, a $C_3$–$C_{12}$-cycloalkyl group, a $C_7$–$C_{12}$-aralkyl group or a mono- or bi-nuclear aryl group.

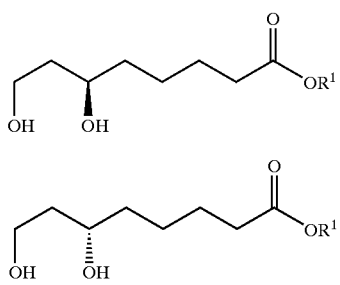

The invention relates also to novel compounds of formulae II and III, which are used as starting compounds or intermediates in the synthesis of the compounds (R)-I and (S)-I.

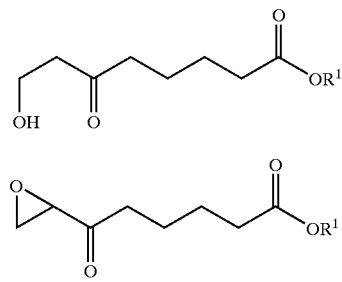

PRIOR ART

The compounds (R)-I and (S)-I are known. They are both used predominantly as intermediates for the synthesis of enantiomerically pure α-lipoic acid of formula IV and its derivatives. α-Lipoic acid is 1,2-dithiolane-3-pentanoic acid (thioctic acid).

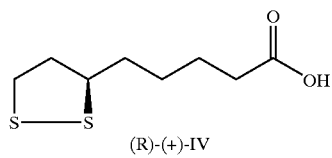

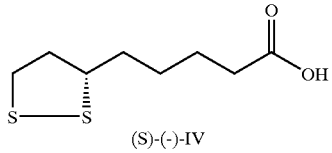

The (R)-enantiomer of α-lipoic acid (R)-(+)-IV is a natural substance which occurs in small concentrations in virtually all animal and vegetable cells. α-Lipoic acid is of crucial importance as a coenzyme in the oxidative decarboxylation of α-ketocarboxylic acids (e.g. pyruvic acid). α-Lipoic acid is pharmacologically active and has antiphlogistic and antinociceptive (analgesic) properties, as well as cytoprotective properties. An important medicinal indication of racemic α-lipoic acid is the treatment of diabetic polyneuropathy. According to more recent results (A. Baur et al., Klin. Wochenschr. 1991, 69, 722; J. P. Merin et al., FEBS Lett. 1996, 394, 9) α-lipoic acid may possibly gain importance in the control of diseases caused by HIV-1 and HTLV IIIB viruses.

In the case of the pure optical isomers of α-lipoic acid (R- and S-form, i.e (R)-α-lipoic acid and (S)-α-lipoic acid), in contrast to the racemate, the (R)-enantiomer, has predominantly antiphlogistic activity and the (S)-enantiomer has predominantly antinociceptive activity (EP 0427247, 08.11.90). The two enantiomers have also been found to have different pharmacokinetic properties (R. Hermann et al., Eur. J. Pharmaceut. Sci. 1996, 4, 167; G. Raddatz and H. Bisswanger, J. Biotechnol. 1997, 58, 89; T. M. Hagen et al., FASEB J. 1999, 13, 411). The synthesis of the pure enantiomers is therefore of great importance.

Known processes for preparing enantiomerically pure (α-lipoic acids include racemate cleavage of α-lipoic acid or its precursors, asymmetric syntheses using chiral auxiliaries, chiral pool syntheses using naturally occurring optically active starting compounds, and also microbial syntheses (overview article: J. S. Yadav et al., J. Sci. Ind. Res. 1990, 49, 400; and also: E. Walton et al., J. Am. Chem. Soc. 1955, 77, 5144; D. S. Acker and W. J. Wayne, J. Am. Chem. Soc. 1957, 79, 6483; L. G. Chebotareva and A. M. Yurkevich, Khim.-Farm. Zh. 1980, 14, 92; A. S. Gopalan et al., Tetrahedron Lett. 1989, 5705; A. G. Tolstikov et al., Bioorg. Khim. 1990, 16, 1670; L. Dasaradhi et al., J. Chem. Soc., Chem. Commun. 1990, 729; A. S. Gopalan et al., J. Chem. Perkin Trans. 1 1990, 1897; EP 0487986 A2, 14.11.91; R. Bloch et al., Tetrahedron 1992, 48, 453; B. Adger et al., J. Chem. Soc., Chem. Commun. 1995, 1563; DE-OS 19533881.1, 13.09.95; DE-OS 19533882.1, 13.09.95; Y. R. Santosh Laxmi and D. S. Iyengar, Synthesis, 1996, 594; M. Bezbarua et al., 1996, 1289; N. W. Fadnavis et al., Tetrahedron: Asymmetry 1997, 8, 337; N. W. Fadnavis et al., Tetrahedron: Asymmetry 1998, 9, 4109; S. Lee and Y. Ahn, J. Korean Chem. Soc. 1999, 43, 128).

Of those processes, racemate cleavage via the formation of diastereoisomeric salts of α-lipoic acid with optically active α-methylbenzylamine (DE-OS 4137773.7, 16.11.91 and DE-OS 4427079.8, 30.07.94) represents the most economical variant hitherto. However, because the racemate separation does not take place until the last stage of the synthesis sequence, high yields cannot be achieved.

The known chemocatalytic asymmetric processes for the preparation of enantiomerically pure α-lipoic acid (DE-OS 3629116.1, 27.08.86; DE-OS 19709069.1, 6.03.97; R. Zimmer et al., Tetrahedron: Asymmetry 2000, 11, 879) are uneconomical because of the high costs of the starting compounds.

The object of the invention is, therefore, to make available, as desired, the 6,8-dihydroxyoctanoic acid esters (R)-I and (S)-I leading to the two enantiomers of α-lipoic acid, in a high chemical and optical space-time yield using inexpensive starting materials.

DESCRIPTION OF THE INVENTION

According to the invention, that is achieved by asymmetric chemocatalytic hydrogenation of 8-hydroxy-6-oxo-octanoic acid esters of formula II, in which $R^1$ represents a $C_1$–$C_{20}$-alkyl group, a $C_3$–$C_{12}$-cycloalkyl group, a $C_7$–$C_{12}$-aralkyl group or a mono- or bi-nuclear aryl group, in the presence of complexes consisting of ruthenium and optically active phosphines.

The compounds II are novel and can be obtained by selective hydrogenation of the 7,8-epoxy-6-oxo-octanoic acid esters III, preferably in the presence of platinum, palladium or nickel catalysts.

The preparation of the 7,8-epoxy-6-oxo-octanoic acid esters III, which are also novel, is possible in high yields by epoxidation of 6-oxo-7-octenoic acid esters of formula V, preferably by means of sodium percarbonate in methanol. The compounds V are known and are obtainable by elimination of hydrogen chloride from 8-chloro-6-oxo-octanoic acid esters, which are used as inexpensive starting compounds for the commercial synthesis of racemic α-lipoic acid (M. W. Bullock et al., J. Am. Chem. Soc. 1954, 76, 1828).

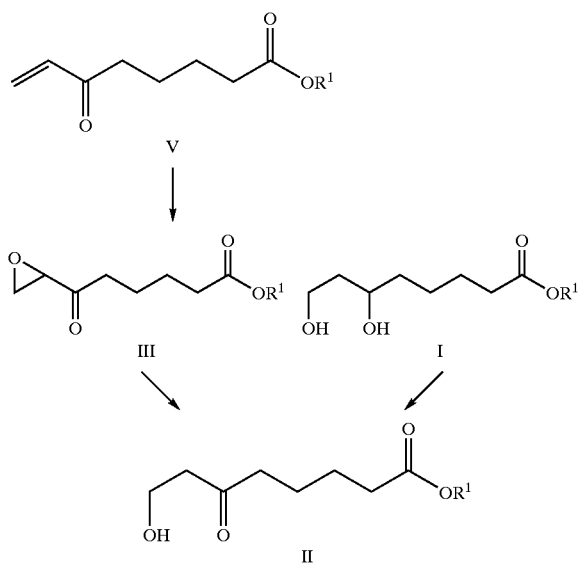

Alternatively, racemic 6,8-dihydroxyoctanoic acid esters of formula I can be converted into compounds of formula II by regioselective oxidation of the secondary hydroxy group, preferably by means of sodium hypochlorite in acetic acid. The preparation of racemic 6,8-dihydroxyoctanoic acid esters of formula I is known and can be carried out, inter alia, starting from butadiene and acetic acid (J. Tsuji et al., J. Org. Chem. 1978, 43, 3606).

Ruthenium-diphosphine complexes are of particular interest as catalysts for the asymmetric hydrogenation of the compounds II. As typical but non-limiting examples there may be mentioned the ruthenium complexes of the following formulae VI to XII:

| | |
|---|---|
| $[RuHal_2D]_n(L)_x$ | VI |
| $[RuHal AD]^+Y^-$ | VII |
| $RuD_n OOCR^2 OOCR^3$ | VIII |
| $[RuH_xD_n]^{m+}Y_m^-$ | IX |
| $[RuHal\ (PR^4{}_2R^5)D]^{2+}Hal_2^-$ | X |
| $[RuHHalD_2]$ | XI |
| $[DRu\ (acac)_2]$ | XII | wherein:

acac represents acetyl acetonate,

D represents a diphosphine of the general formula XIII,

Hal represents halogen, especially iodine, chlorine or bromine, $R^2$ and $R^3$ are the same or different and represent alkyl having up to 9 carbon atoms, preferably up to 4 carbon atoms, which is optionally substituted by halogen, especially fluorine, chlorine or bromine, or represent phenyl which is optionally substituted by alkyl having from 1 to 4 carbon atoms, or represent an α-aminoalkyl acid having preferably up to 4 carbon atoms, or together form an alkylidene group having up to 4 carbon atoms, $R^4$ and $R^5$ are the same or different and represent optionally substituted phenyl, preferably substituted by alkyl having from 1 to 4 carbon atoms or by halogen, Y represents Cl, Br, I, $ClO_4$, $BF_4$ or $PF_6$, A represents an unsubstituted or substituted benzene ring, such as p-cymene, L represents a neutral ligand such as acetone, a tertiary amine or dimethylformamide, n and m each represent 1 or 2, x represents 0 or 1, wherein in formula IX n represents 1 and m represents 2 when x=0, and n represents 2 and m represents 1 when x=1.

The complexes of formulae VI to XII can be prepared by methods known per se (VI and XI: EP 174057 and J. P. Genet et al., Tetrahedron Asymmetry 1994, 5, 675; VII: EP 366390; VII: EP 245959 and EP 272787; IX: EP 256634; X: EP 470756; XII: P. Stahly et al., Organometallics 1993, 1467).

As optically active diphosphine ligands there are used compounds of the general formula XIII:

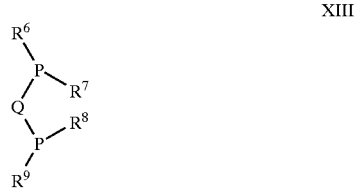

XIII wherein:

Q represents a group bridging the two P atoms and having from 2 to 24 carbon atoms and optionally from 1 to 4 hetero atoms, preferably O, S, N and Si, the bridging being formed by at least 2 of the carbon atoms and optionally from 1 to 4 of the hetero atoms, $R^6$–$R^9$ are the same or different and represent alkyl groups having from 1 to 18 carbon atoms, cycloalkyl groups having from 5 to 7 carbon atoms or aryl groups having from 6 to 12 carbon atoms.

The following ligands may be mentioned as examples of particularly preferred chiral diphosphines used in enantiomerically pure form:

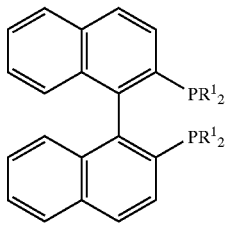

BINAP: R¹ = Phenyl
Tolyl-BINAP: R¹ p-Tolyl

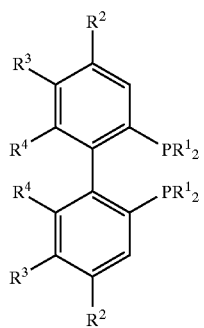

BIMOP: R¹ = Ph, R² = R⁴ = Me, R³ = OMe
FUPMOP: R¹ = Ph, R² = R⁴ = CF₃, R³ = OMe
BIFUP: R¹ = Ph, R² = R⁴ CF₃, R³ = H
BIPHEMP: R¹ = Ph, R² = R³ = H, R⁴ = Me
MeO-BIPHEP: R¹ = Ph, R² = R³ = H, R⁴ = OMe
BICHEP: R¹ = c-C₆H₁₁, R² = R³ = H, R⁴ = Me

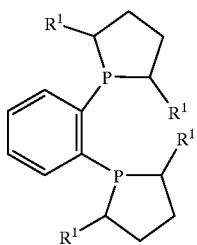

Me-DuPHOS: R¹ = Me
Et-DuPHOS: R¹ = Et

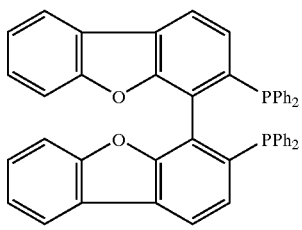

BIBFUP

-continued

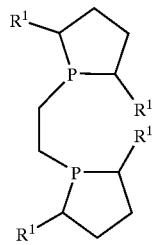

Me-BPE: R¹ = Me
iPr-BPE: R¹ = iPr

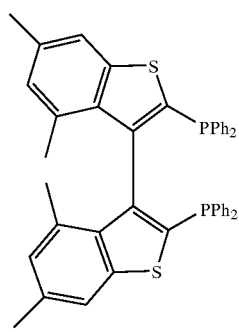

XIV

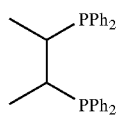

CHIRAPHOS

The ligands listed above as racemic structures for the sake of simplicity are compounds that are known in their enantiomerically pure forms (BINAP: R. Noyori et al., J. Am. Chem. Soc. 1980, 102, 7932; BIMOP, FUPMOP, BIFUP: M. Murata et al., Synlett 1991, 827; BIBHEMP: R. Schmid et al., Helv. Chim. Acta 1988, 71, 697; MeO-BIPHEP: R. Schmid et al., Helv. Chim. Acta 1991, 74, 370; BICHEP: A. Miyashita et al., Chem. Lett. 1989, 1849; DuPHOS: M. Burk et al., Organometallics 1990, 9, 2653; BPE: M. Burk et al., J. Am. Chem. Soc. 1995, 117, 4423; BIBFUP: EP 643065; CHIRAPHOS: B. Bosnich et al., J. Am. Chem. Soc. 1977, 99, 6262; XIV: WO 96/01831).

The asymmetric hydrogenation of the compounds of formula II in the presence of the above-described optically active ruthenium-diphosphine complexes of formulae VI to XII can be carried out in suitable organic solvents that are inert under the reaction conditions. Special mention may be made as such solvents of alcohols, such as methanol or ethanol, chlorinated hydrocarbons, such as methylene chloride or dichloroethane, cyclic ethers, such as tetrahydrofuran or dioxane, esters, such as, for example, ethyl acetate, aromatic hydrocarbons, such as benzene or toluene, or also mixtures thereof and the like. In order to suppress possible ketal formation when working in alcohols as solvent, up to 10 vol. % water can be added. The substrate concentrations are preferably from 5 to 50 vol. %, especially from 20 to 40 vol. %.

The reactions can preferably be carried out at temperatures of approximately from 10° C. to 140° C., especially approximately from 20° C. to 70° C., and under a hydrogen pressure of approximately from 1 to 100 bar, especially from 4 to 50 bar. The reaction times are generally from 2 to 48 hours, mostly from 6 to 24 hours. The molar ratio between ruthenium in the complexes VI to XII and the compounds II to be hydrogenated is advantageously from approximately 0.001 to approximately 5 mol %, preferably from approximately 0.005 to approximately 0.2 mol %.

In the reaction, the desired enantiomer of formula I can be obtained by choosing the optically active diphosphine ligand of formula XIII having the appropriate configuration. Accordingly, the use of (R)-(+)-BINAP, for example, yields products of formula (R)-I, and the use of (S)-(−)-BINAP yields products of formula (S)-I.

The compounds (S)-I and (R)-I are used to prepare the enantiomerically pure α-lipoic acids of formula IV by, in known manner (J. D. Gopalan et al., Tetrahedron Lett. 1985, 2535):

a) converting those compounds, in organic solution, with a sulfonic acid chloride and a tertiary nitrogen base, into the bissulfonic acid ester of I, b) reacting that compound, in a polar solvent, with sulfur and an alkali metal sulfide to form the α-lipoic acid ester, and c) if desired, converting that ester into the respective pure enantiomer of α-lipoic acid. In that process, the compounds (R)-I yield (S)-(−)-α-lipoic acid and the compounds (S)-I yield (R)-(+)-α-lipoic acid.

The compounds (R)-I and (S)-I and (R)-(+)-IV and (S)-(−)-IV prepared by the process according to the invention generally have a high enantiomeric excess, corresponding to an optical yield of from 90 to 99%.

The enantiomeric ratios are measured directly by chiral HPLC or GC on optically active columns.

By means of the present invention it is possible to make available, in an economical manner and in high chemical and optical yields, the enantiomerically pure 6,8-dihydroxy-octanoic acid esters of the general formula I ($R^1=C_1-C_{20}$-alkyl, $C_3-C_{12}$-cycloalkyl, $C_7-C_{12}$-aralkyl or mono- or bi-nuclear aryl) as intermediates for the preparation of the enantiomerically pure α-lipoic acids of formula IV.

The Examples which follow illustrate but do not limit the invention.

EXAMPLE 1

43.5 mg (0.087 mmol) of $[RuCl_2(C_6H_6)]_2$, 113.7 mg (0.183 mmol) of (R)-BINAP and 3 ml of dimethylformamide were placed into a 20 ml Schlenk flask under Argon. The reddish-brown suspension was heated for 10 minutes at 100° C. The solution, which was then clear, was cooled and concentrated in vacuo (1 to 0.1 mmHg) at 50° C. with vigorous stirring over a period of 1 hour. The orange-brown solid that remained was taken up in 1 ml of tetrahydrofuran and was used in that form as a Ru-(R)-BINAP catalyst in the asymmetric hydrogenations.

EXAMPLE 2

43.5 mg (0.087 mmol) of $[RuCl_2(C_6H_6)]_2$, 113.7 mg (0.183 mmol) of (S)-BINAP and 3 ml of dimethylformamide were placed into a 20 ml Schlenk flask under Argon. The reddish-brown suspension was heated for 10 minutes at 100° C. The solution, which was then clear, was cooled and concentrated in vacuo (1 to 0.1 mmHg) at 50° C. with vigorous stirring over a period of 1 hour. The orange-brown solid that remained was taken up in 1 ml of tetrahydrofuran and was used in that form as a Ru-(S)-BINAP catalyst in the asymmetric hydrogenations.

EXAMPLE 3

A 100 ml autoclave was charged under argon with 3.8 g (20 mmol) of 8-hydroxy-6-oxo-octanoic acid methyl ester, with the Ru-(R)-BINAP catalyst solution prepared under Example 1, and with 20 ml of oxygen-free methanol. The hydrogenation was carried out for 20 hours at 60° C., at a constant pressure of 40 bar pure $H_2$ and with intensive stirring. When the reaction was complete, the solvent was distilled off using a rotary evaporator. Purification of the residue by column chromatography (silica gel, ethyl acetate/n-hexane) yielded 3.2 g (85%) of (R)-6,8-dihydroxyoctanoic acid methyl ester having an enantiomeric excess of 96% (chiral GC).

EXAMPLE 4

A 100 ml autoclave was charged under argon with 3.8 g (20 mmol) of 8-hydroxy-6-oxo-octanoic acid methyl ester, with the Ru-(S)-BINAP catalyst solution prepared under Example 2, and with 20 ml of oxygen-free methanol. The hydrogenation was carried out for 20 hours at 60° C., at a constant pressure of 40 bar pure $H_2$ and with intensive stirring. When the reaction was complete, the solvent was distilled off using a rotary evaporator. Purification of the residue by column chromatography (silica gel, ethyl acetate/n-hexane) yielded 3.1 g (82%) of (S)-6,8-dihydroxyoctanoic acid methyl ester having an enantiomeric excess of 96% (chiral GC).

EXAMPLE 5

100 ml of aqueous sodium hypochlorite solution (10–13% active chlorine) were added dropwise at room temperature, over a period of 45 minutes, to 16.6 g (87 mmol) of 6,8-dihydroxyoctanoic acid methyl ester in 200 ml of glacial acetic acid. After stirring for a further 3 hours at room temperature, 180 ml of isopropanol were added in order to destroy excess sodium hypochlorite, and stirring was carried out for 10 minutes. The reaction mixture was then added to 1200 ml of water and extracted several times with methylene chloride. The combined organic phases were washed with cold-saturated sodium hydrogen carbonate solution. After drying over sodium sulfate, the solvent was distilled off using a rotary evaporator. 13.0 g (80%) of 8-hydroxy-6-oxo-octanoic acid methyl ester were obtained.

$^{13}C$ NMR ($CDCl_3$): δ=23.4, 25.3, 34.0, 42.8, 45.2, 51.7, 57.9, 174.1, 211.0

EXAMPLE 6

A 100 ml autoclave was charged under argon with 9.4 g (50 mmol) of 7,8-epoxy-6-oxo-octanoic acid methyl ester, with 0.4 g of platinum(IV) oxide catalyst, and with 50 ml of ethyl acetate. The hydrogenation was carried out for 16 hours at 20° C., at a constant pressure of 50 bar pure $H_2$ and with intensive stirring. When the reaction was complete, the catalyst was filtered off and the solvent was distilled off using a rotary evaporator. Purification of the residue by column chromatography (silica gel, ethyl acetate/n-hexane) yielded 6.3 g (67%) of 8-hydroxy-6-oxo-octanoic acid methyl ester.

EXAMPLE 7

39.1 g (250 mmol) of sodium percarbonate were added in four portions at room temperature, over a period of 2 hours, with stirring, to 13.9 g (82 mmol) of 6-oxo-7-octenoic acid methyl ester in 210 ml of methanol. After stirring for a further one hour at room temperature, the reaction mixture was added to 1000 ml of water and extracted several times with methylene chloride. The combined organic phases were washed with water. After drying over sodium sulfate, the solvent was distilled off using a rotary evaporator. 13.5 g (88%) of 7,8-epoxy-6-oxo-octanoic acid methyl ester were obtained.

$^{13}$C NMR (CDCl$_3$): δ=21.8, 23.2, 32.4, 41.5, 50.1, 57.4, 66.5, 172.5, 207.4

What is claimed is:

1. Process for the preparation of compounds of the general formula I

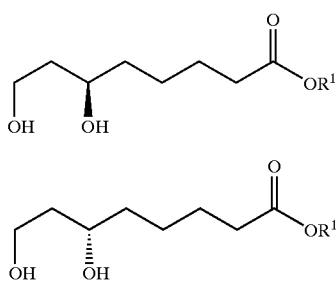

in which R$^1$ represents a C$_1$–C$_{20}$-alkyl group, a C$_3$–C$_{12}$-cycloalkyl group, a C$_7$–C$_{12}$-aralkyl group or a mono- or bi-nuclear aryl group, wherein a ketone of formula II

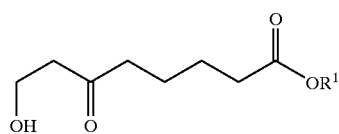

in which R$^1$ is as defined above, is subjected to asymmetric hydrogenation.

2. Process according to claim 1, wherein the asymmetric hydrogenation is carried out in the presence of a ruthenium-diphosphine complex of formulae VI to XII:

| | |
|---|---|
| [RuHal$_2$D]$_n$ (L)$_x$ | VI |
| [RuHalAD]$^+$Y$^-$ | VII |
| RuD$_n$OOCR$^2$OOCR$^3$ | VIII |
| [RuH$_x$D$_n$]$^{m+}$Y$_m^-$ | IX |
| [RuHal (PR$^4_2$R$^5$)D]$^{2+}$Hal$_2^-$ | X |
| [RuHHalD$_2$] | XI |
| [DRu (acac)$_2$] | XII | wherein:
acac represents acetyl acetonate,
D represents a diphosphine of the general formula XIII,
Hal represents halogen,
R$^2$ and R$^3$ are the same or different and represent alkyl having up to 9 carbon atoms, which is optionally substituted by halogen, or represent phenyl which is optionally substituted by alkyl having from 1 to 4 carbon atoms, or represent an α-aminoalkyl acid having up to 4 carbon atoms, or together form an alkylidene group having up to 4 carbon atoms,
R$^4$ and R$^5$ are the same or different and represent optionally substituted phenyl,
Y represents Cl, Br, I, ClO$_4$, BE$_4$ or PF$_6$,
A represents an unsubstituted or substituted benzene ring,
L represents a neutral ligand
n and m each represent 1 or 2,
x represents 0 or 1, wherein in formula IX n represents 1 and m represents 2 when x=0, and n represents 2 and m represents 1 when x=1 and as the optically active diphosphine ligands D are compounds of the general formula XIII

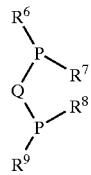

wherein:

Q represents a group bridging the two P atoms and having from 2 to 24 carbon atoms and optionally from 1 to 4 hetero atoms, the bridging being formed by at least 2 of the carbon atoms and optionally from 1 to 4 of the hetero atoms, R$^6$–R$^9$ are the same or different and represent alkyl groups having from 1 to 18 carbon atoms, cycloalkyl groups having from 5 to 7 carbon atoms or aryl groups having from 6 to 12 carbon atoms.

3. Process according to claim 1, wherein the asymmetric hydrogenation is carried out at temperatures of from approximately 10° C. to approximately 140° C. and under a pressure of approximately from 1 to 100 bar.

4. Process according to claim 1, wherein the asymmetric hydrogenation is carried out with reaction times of from 2 to 48 hours with a molar ratio between ruthenium in complexes VI to XII and the compounds II to be hydrogenated are approximately 0.001 to approximately 5 mol %.

5. 8-Hydroxy-6-oxo-octanoic acid esters of the general formula II

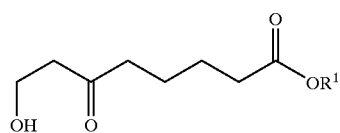

in which R$^1$ represents a C$_1$–C$_{20}$-alkyl group, a C$_3$–C$_{12}$-cycloalkyl group, a C$_7$–C$_{12}$-aralkyl group or mono- or bi-nuclear aryl group.

6. 7,8-Epoxy-6-oxo-octanoic acid esters of the general formula III

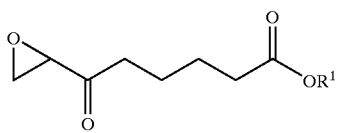

in which R$^1$ represents a C$_1$–C$_{20}$-alkyl group, a C$_3$–C$_{12}$-cycloalky group, a C$_7$–C$_{12}$-aralkyl group or a mono- or bi-nuclear aryl group.

7. Process for the preparation of (R)-(+)-α-lipoic acid of formula (R)-(+)-IV

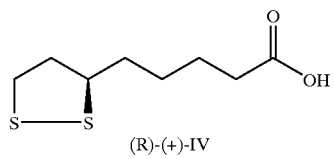

(R)-(+)-IV

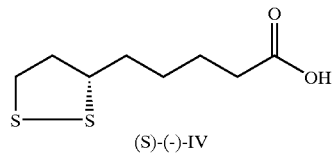

(S)-(-)-IV wherein the compounds II according to claim 1 are subjected to asymmetric hydrogenation to form the compounds (S)-I, and said compounds,
  a) are converted, in organic solution, with a sulfonic acid chloride and a tertiary nitrogen base, into the bissulfonic acid ester of (S)-I,
  b) the compound obtained in step a) is reacted, in a polar solvent, with sulfur and an alkali metal sulfide to form the (R)-(+)-α-lipoic acid ester, and
  c) that ester is, optionally, converted into (R)-(+)-α-lipoic acid.

8. Process for the preparation of (S)-(−)-α-lipoic acid of formula (S)-(−)-IV wherein the compounds II according to claim 1 are subjected to asymmetric hydrogenation to form the compounds (R)-I, and said compounds,
  a) are converted, in organic solution, with a sulfonic acid chloride and a tertiary nitrogen base, into the bissulfonic acid ester of (R)-I,
  b) the compound obtained in step a) is reacted, in a polar solvent, with sulfur and an alkali metal sulfide to form the (S)-(−)-α-lipoic acid ester, and
  c) that ester is, optionally, converted into (S)-(−)-α-lipoic acid.

* * * * *